US012599341B2

(12) United States Patent
Shah

(10) Patent No.: US 12,599,341 B2
(45) Date of Patent: Apr. 14, 2026

(54) AUTONOMOUS, CONSENT DRIVEN AND GENERATIVE DEVICE, SYSTEM AND METHOD THAT PROMOTES USER PRIVACY, SELF-KNOWLEDGE AND WELL-BEING

(71) Applicant: Mihir Shah, Chester Springs, PA (US)

(72) Inventor: Mihir Shah, Chester Springs, PA (US)

( * ) Notice: Subject to any disclaimer, the term of this patent is extended or adjusted under 35 U.S.C. 154(b) by 0 days.

(21) Appl. No.: 19/217,216

(22) Filed: May 23, 2025

(65) Prior Publication Data

US 2025/0359827 A1    Nov. 27, 2025

Related U.S. Application Data

(60) Provisional application No. 63/773,735, filed on Mar. 18, 2025, provisional application No. 63/656,718, filed on Jun. 6, 2024, provisional application No. 63/651,543, filed on May 24, 2024.

(51) Int. Cl.
| | |
|---|---|
| *A61B 5/117* | (2016.01) |
| *A61B 5/00* | (2006.01) |
| *A61B 5/16* | (2006.01) |
| *G06F 3/01* | (2006.01) |
| *H04W 12/06* | (2021.01) |

(52) U.S. Cl.
CPC .............. *A61B 5/744* (2013.01); *A61B 5/117* (2013.01); *A61B 5/165* (2013.01); *G06F 3/011* (2013.01); *H04W 12/06* (2013.01)

(58) Field of Classification Search
CPC ....................................................... G06F 3/017
See application file for complete search history.

(56) References Cited

U.S. PATENT DOCUMENTS

| | | | |
|---|---|---|---|
| 12,148,014 B1 * | 11/2024 | Bini ........................ | G06N 20/00 |
| 2022/0407853 A1 * | 12/2022 | Henry .................... | G06N 20/00 |
| 2023/0214470 A1 * | 7/2023 | Tily ................. | G06Q 20/40145 |
| | | | 726/17 |
| 2023/0377023 A1 * | 11/2023 | Buzzell .............. | G06Q 30/0641 |

FOREIGN PATENT DOCUMENTS

| | | | | | |
|---|---|---|---|---|---|
| CN | 117503133 A | * | 2/2024 | ............. | G16H 40/63 |
| CN | 117785350 A | * | 3/2024 | | |
| KR | 20250104674 A | * | 7/2025 | ............. | G16H 50/30 |
| WO | WO-2023049197 A1 | * | 3/2023 | ........... | G01C 21/206 |

* cited by examiner

*Primary Examiner* — Di Xiao
(74) *Attorney, Agent, or Firm* — Riverside Law LLP

(57) ABSTRACT

An apparatus, system and method for improving well-being. Included are: a plurality of satellite slave processors associated with satellite devices, each having operatively communicative therewith a dedicated operating system (DOS) comprising non-transitory computing code; at least one first master device including at least one personal functions processor having operatively communicative therewith a personal functions operating system (PFOS) comprising non-transitory computing code; and at least one of the PFOS being capable of commanding the DOS and others of the PFOS, and thereby being capable of accessing and controlling data and applications provided by both the satellite slave processors and the others of the at least one personal functions processor.

25 Claims, 7 Drawing Sheets

AUTONOMOUS, CONSENT DRIVEN AND GENERATIVE DEVICE, SYSTEM AND METHOD THAT PROMOTES USER PRIVACY, SELF-KNOWLEDGE AND WELL-BEING

CROSS-REFERENCE TO RELATED APPLICATIONS

This application claims priority to U.S. Provisional Application No. 63/773,735 filed on Mar. 18, 2025, U.S. Provisional Application No. 63/656,718 filed on Jun. 6, 2024, and U.S. Provisional Application No. 63/651,543 filed on May 24, 2024, each of which is incorporated herein by reference in their entirety.

BACKGROUND OF THE DISCLOSURE

Field of the Invention

The disclosure relates to the field of mobile devices, and, more particularly, to a device, system and method for a mobile device that promotes privacy, self-knowledge and well-being.

Description of the Background

In the economy of the modern mobile device, the most valuable commodity is the human user, and the data generated from and by each user. This most valuable commodity is generally provided by the user for free and, in some cases, the user even pays for some goods or service while providing this valuable data for free.

An individuals' well-being and self-knowledge depend on one another. "The examined life" is one of man's greatest gifts. It helps a person improve themself by being conscious of themself, becoming aware of their patterns of thinking and acting, their way of conducting themself in the world. If an individual does this diligently, they can become aware of behaviors that may thwart the advancement of their own life, and the lives of fellow human beings.

Smart technology has not enriched this project. Although mobile devices were promoted with the promises that they would make lives better, provide autonomy, give access to more knowledge, enable one to make better use of time and energy, and allow one to fulfill their potential, these promises have been broken; technology has complicated the world without adding to human wisdom, and so have made one more dangerous to themself. Technology has magnified individuals' impulses while reducing the forces of time, distance and difficulty that regulate them. It has made one's thinking more dissociative and distractible, and made sociability more narcissistic and less intimate. It had multiplied possibilities so much that often one cannot make choices soundly. It has created so many competing stories that one cannot tell which are real. It has created so many self-appointed authorities that one does not know which to trust. Through mobile devices, the world looks like a funhouse of refracted light and mirrors. It moves through an individual so rapidly, that one must work harder just to stay in one place. So individuals feel burnout instead of progress, a sense of futility, and frustration about the whole situation: all of this technological abundance could be helping humanity, if only one knew how to harness it.

The idea of the human being has somehow become smaller. Humans have been capable of great feats throughout history. Humans built mind palaces of memory, and opened vast spaces inside to explore and create. But as the smartphone has rooted itself, it has made it harder to separate oneself as human being from technological appendages [Konok, V., Pogány, Á. and Miklósi, Á., 2017. Mobile attachment: Separation from the mobile phone induces physiological and behavioural stress and attentional bias to separation-related stimuli. Computers in Human Behavior, 71, pp. 228-239]. The mobile device—in particular the smartphone, has become humanity's default way of idling, socializing, and solving problems. When an individual is caught without their mobile device(s), they feel severed from themself. This dependence is reflexive, and often gives a constant feeling of anxiety, of being powerless and naked, on their own. Even when an individual is aware of its dangers, one usually cannot bring themself to act; as one does not feel that they have any alternative to choose. Humans live in this double bind, and it makes an individual feel less like a human being and more like a restless beast. As the philosopher Martin Heidegger famously warned, technology is not fitting into the frame of the human being; the individual is being remade to fit into its frame, and is finding themself shrinking in the process [Heidegger, Martin. "The question concerning technology." (1993)].

Through humanity's use of apps, subscriptions, and various commercial activities on mobile devices, personal data is extracted from individuals. Many of the most intimate details of personal lives—health, habits, hobbies, moods, taste in food, art and sex—are given to parties that do not care for individuals or humanity, that then use or sell the data to others to manipulate or nudge human behavior to sell their products or favored political candidates or positions. In return, individuals receive the convenience from the use of various apps, but lose the benefit of the knowledge that could be gleaned from the individuals' data. If aggregated, this knowledge could be powerful, and frightening. An individual's browser histories can reveal the objects of one's interests and desires; keystrokes and speech patterns can reveal one's process of thinking; one's movements can reveal habits, good and bad; and one's biometrics can indicate their heath and temperament. It is now possible to create models and profiles of a person with these trackable metrics, as though humans were naturalists observing a foreign species. One can image a person's physical state, their mental state, and the patterns that make up their life and relationships.

Patterns derived from personal data, meta-data and context are sensitive, and very revealing. If made available to other parties, they leave a person exposed to shame, theft, reductive profiling, manipulation, and a myriad of other harms. This is the environment one finds themself in: a landscape rife with data brokerage and breaches of privacy. Laws around the world have failed to keep up with this problem and provide adequate safeguards. The intuitive significance of privacy has not been properly translated into humanity's ethical consciousness, much less into public policy. And so, the aforementioned double bind: people are both anxious about technology and utterly incapable of choosing against it. This is why privacy is a pivotal concern, not merely to protect a person from concrete harm, but from the psychological danger of being watched. An individuals' digital world is now an extension of the individuals' home. They are their bedrooms, their bathrooms, their living rooms. The presence of interloping eyes affects one's sense of solitude. It affects how honestly one is able to look at oneself, how directly one is able to talk to oneself. How does one ensure that one's data cannot be breached by the outside observer, and give the person the space to breathe and see themself clearly?

One must consider the nature of human data. How should one understand its meaning? Can one frame it in a philosophical way? Finding the right metaphor is often useful for taming technologies. For example, data has often been called the "new oil." Consider this metaphor, and find some revealing features: a crude, flammable resource, something finite and possessable; hardly the best symbol to reflect the fruits of the human spirit. Now consider an alternative metaphor: sunshine. The human being is not just a source of energy, but also of intelligibility—they are a source of light, voice, vision and meaning. The sun is an ancient symbol in philosophy and religious life, a proxy for the limitless part of reality and humanity. It cannot be completely known, or completely tamed. But it gives off a radiance that, if cultivated in modest ways, can be used to light the darker corners of life. Mirrors can light up a room by diffusing a single source of sunlight, without extinguishing that light, or being equal to it. If human data is oil, then the human being can effectively be used up, owned by another party, or put to waste. If data is like sunshine, then each human being is an end in themself, and cannot be exhausted. The data they give off can shed light back on themself without being confused for themself. A mirror does not know the feeling of the sun on its face, but it can still be made to reflect the light, so a person can see themself by the very light they cast. Instead of the funhouse, what if technology could become a reflective surface to harness the interpretive power of one's data and direct it to those places that need one's attention? What insight would become possible for humans, as individuals and as a species, if humans learned to direct data in this way?

An individual creates personal data every time they use their devices and the sensors inside it—when they move, when they speak, type words, take pictures, use apps or talk with centralized large language models on the internet—they are constantly creating Original Personal Data (OPD). Digital devices they use every day, fitted with eyes (cameras), ears (mic), and many other sophisticated sensors (touch, motion, location, etc) are now contributing to constantly learning the user, their digital activity and physical surroundings. Where they are, what they're doing and how fast is their heart racing, are all precisely knowable simultaneously, giving away their deeply Personal Context, derived from the OPD and meta-data, that even the users are not aware of themselves.

Given how much time one spends with, around or in front of the devices (way more than human relatives and friends) it is easily possible to gather one's Ongoing Personal Context (OPC) by learning, analyzing, assessing, or inferring from their OPD and attached meta-data.

While use of connected electronics is at an all-time high—both, intra and inter-user, the user's privacy, safety and security is degrading faster than ever before, making the users vulnerable to theft, breaches, bullshit and burnout. User's and their families find themselves constantly running on a treadmill of technology, becoming more difficult to understand and rapidly evolving, resulting in quintessential double-bind—can't slow down and can't keep up.

User's OPD and OPC are being shaped as the necessary oil to fuel the growth of hyper-personalized digital services in the field of LLM driven AI and its ability to reach AGI.

A great many studies have shown that misery, depression, loneliness, and addiction are at an all-time high. Much of the growth in these adverse human conditions stems from the isolation and stress caused by society's extreme use of electronics, and particularly the use of personal mobile devices. As such, users are constantly providing extremely valuable data to providers of mobile device services, and further paying providers of mobile device services, in exchange for constant increases in negative feelings and emotions.

Moreover, the prevalent use of mobile devices, and the online society that mobile devices enable, often negates any feelings of happiness, achievement and success. For example, each success in life, such as a promotion at a job, graduation from a school, or the buying of a new car, simply elicits comparison to others online. When a mobile device user's family goes on a wonderful vacation to a 3 star hotel in Florida, only to see via app-postings that their neighbors have gone on a far more exotic vacation at a 5 star hotel in Bali, the mobile device user cannot help but feel like her great vacation was a failure, and that she is lesser than her neighbors for having taken her family on that lesser vacation. Accordingly, even successes feel like failures for most users nowadays, and, instead of being celebrated, each new success leaves users wanting more and even greater success to "keep up with the Joneses".

Of course, this problem is exacerbated by the issue that much of what is posted in the online universe afforded by modern mobile devices is exaggerated by the poster, or worse yet is completely untrue. As such, the pervasive feelings of inadequacy and failure experienced by many users are, in reality, based on untruths told by other users to remedy their own feelings of inadequacy and failure.

In our modern mobile device driven society, one's emotional state and sense of self-worth are often dictated by what one sees in the online universe available on mobile devices. That is, the mobile device technology that was created to serve human-kind has now, in essence, enslaved the emotions and well-being of human kind.

Yet further, the mobile device makers and the app-providers, because they are dependent on the free data provided by users for profit, are incentivized to enhance this enslavement, rather than remedy it. Thereby, powerful devices that were initially created to enhance human wisdom, to make humans more efficient and more wise, and to entertain humans, have now led to a universe in which entities profit from human misery and addiction centered on those same powerful devices. And this profit is based on the free data that users provide, and that those profiting entities receive, with those entities capturing and manipulating only that free data that serves their profitability, rather than making any use of data that might solve the increases in human misery and addiction.

SUMMARY OF THE DISCLOSURE

The disclosure is and includes at least devices, systems, and methods of providing and operating mobile devices. More specifically, included in the disclosure is a mobile device, including: a mobile device processor, having operatively communicative therewith a mobile device operating system (MDOS) comprising non-transitory computing code; and a personal functions processor, having operatively communicative therewith a personal functions operating system (PFOS) comprising non-transitory computing code; wherein the PFOS is capable of commanding the MDOS, and is thus capable of accessing and controlling data and applications provided by both the mobile device processor and the personal functions processor. The PFOS accesses and controls at least: mobile device sensors providing sensor data; a plurality of the applications comprising mobile device applications; and a plurality of the applications comprising well-being applications dedicated to developing a wholistic virtual personal avatar from the sensor data and data of the mobile device applications, and to enhancing mental, emotional and physical well-being of a user of the mobile device.

Also included in the disclosure is a PFOS comprising non-transitory computing code configured to develop and modify a wholistic virtual personal avatar of a user of a mobile device without training external from the mobile device, the mobile device comprising dual processors, a master one of the dual computing processors being controlled, and controlling the slave one of the dual computing processors, in accordance with the wholistic virtual personal avatar. The PFOS includes a listen and learn module configured to monitor at least: bio-sensors controlled by the slave processor; visual and audio inputs of the mobile device; electronic activity on the mobile device by the user; global positioning system (GPS) location of the mobile device; and weather at the GPS location.

The PFOS also includes a baseline development module configured to develop a baseline of mental, emotional, and physical states of the user based at least on averages of the monitoring by the listen and learn module, and configured to discern variations from the baseline as deltas. The PFOS further includes a feedback module configured to monitor the listen and learn module and the baseline development module, and to assess therefrom activities by the user on the mobile device that cause the deltas, an extent of the deltas so caused, and prospective remedial actions of which the mobile device is capable to address the deltas and return the user at least to the baseline.

Yet further, the disclosure is and includes a mobile device that includes: a mobile device processor, having operatively communicative therewith a mobile device operating system (MDOS) comprising non-transitory computing code; and a personal functions processor, having operatively communicative therewith a personal functions operating system (PFOS). The PFOS comprises non-transitory computing code configured to develop and modify a wholistic virtual personal avatar of a user of the mobile device by perform listening and learning by monitoring at least: bio-sensors controlled by the mobile device processor; visual and audio inputs of the mobile device; and electronic activity on the mobile device by the user. The PFOS is also configured to log the user into the mobile device solely based on recognizing, by the PFOS, that an attempted log-in includes features known by the PFOS to be indicative specifically of the wholistic virtual personal avatar.

Still further, the disclosure is and includes a system, comprising: a plurality of satellite slave processors associated with satellite devices, each having operatively communicative therewith a dedicated operating system (DOS) comprising non-transitory computing code; at least one first master device including at least one personal functions processor having operatively communicative therewith a personal functions operating system (PFOS) comprising non-transitory computing code; and at least one of the PFOS being capable of commanding the DOS and others of the PFOS, and thereby being capable of accessing and controlling data and applications provided by both the satellite slave processors and the others of the at least one personal functions processor. The data and applications include: biometrics sensor data; a plurality of authentication mechanisms authenticating at least a presence of and specific identity of a human user; and a plurality of the applications comprising well-being applications responsive to the human user only upon a valid one of the authenticating.

BRIEF DESCRIPTION OF THE DRAWINGS

The foregoing purposes and features, as well as other purposes and features, will become apparent with reference to the description and accompanying figures below, which are included to provide an understanding of the disclosure and constitute a part of the specification, in which like numerals represent like elements, and in which.

DETAILED DESCRIPTION OF THE DISCLOSURE

Figure 1:
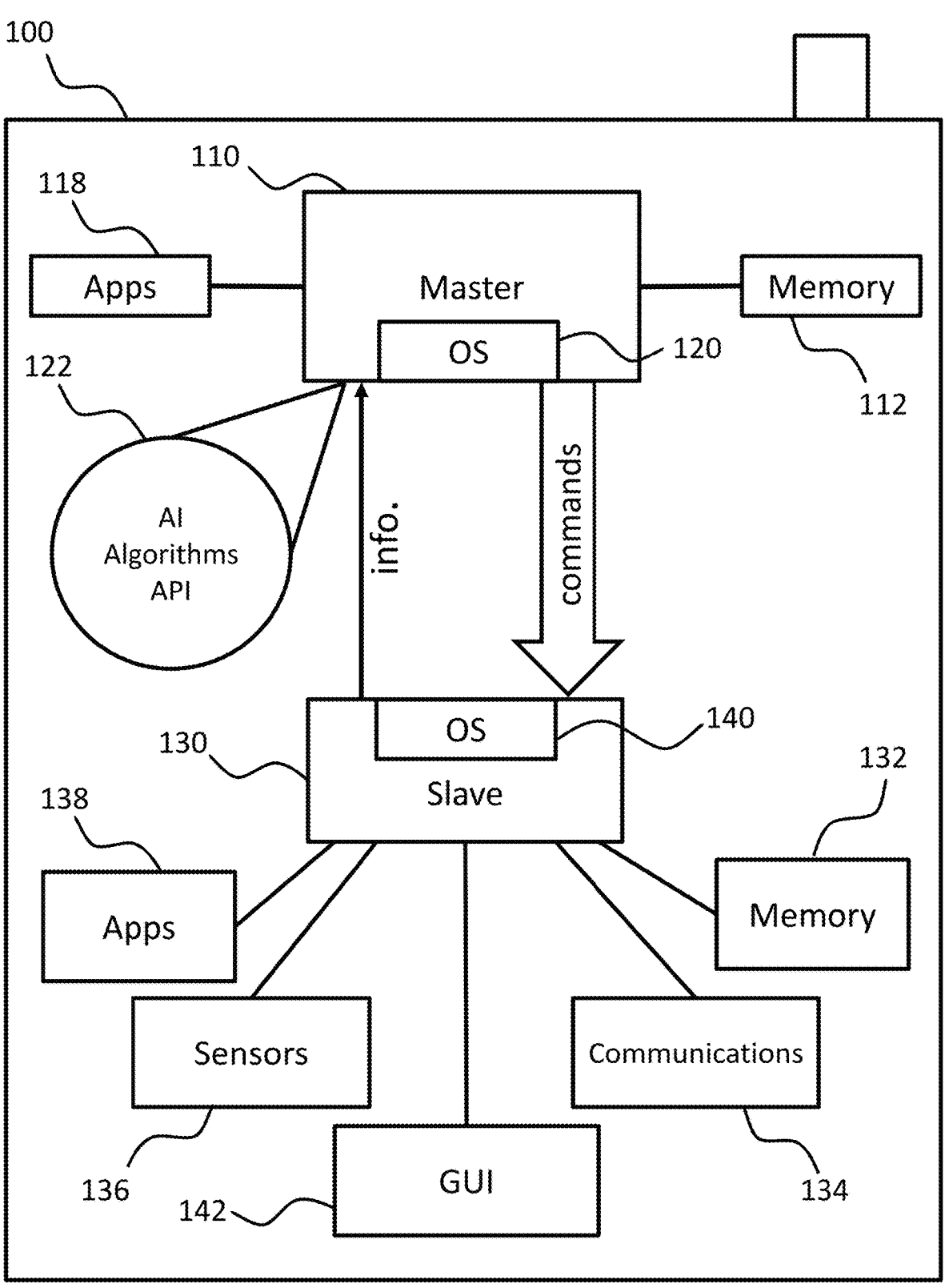
FIG. 1 graphically depicts aspects of the disclosure.

It is to be understood that the figures and descriptions of the present disclosure have been simplified to illustrate elements that are relevant for a clearer comprehension of the present disclosure, while eliminating, for the purpose of clarity, many other elements found in similar systems and methods. Those of ordinary skill in the art may thus recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is nevertheless directed to all such variations and modifications to such elements and methods known to those skilled in the art.

Unless defined otherwise, all technical and scientific terms used herein have the same meaning as commonly understood by one of ordinary skill in the art to which this technical subject matter belongs, and are intended to encompass similar and equivalent terminologies for the subject matters disclosed, unless noted otherwise. And although any methods and materials similar or equivalent to those described herein can be used in the practice or testing of the present disclosure, exemplary methods and materials are described.

As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof.

The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

"About" as used herein when referring to a measurable value such as an amount, a temporal duration, and the like, is meant to encompass variations of ±20%, ±10%, ±5%, ±1%, and ±0.1% from the specified value, as such variations are appropriate. Further, throughout this disclosure various aspects of the disclosure can be presented in a range format. It should be understood that the description in range format is merely for convenience and brevity and should not be construed as an inflexible limitation on the scope of the disclosure. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Processor-implemented modules and systems are disclosed herein that may provide access to and transformation of a plurality of types of digital content, including but not limited to data and data streams, and the algorithms applied herein may track, deliver, manipulate, transform, transceive and report the accessed digital content. Described embodiments of these modules, apps, systems and methods are intended to be exemplary and not limiting.

An exemplary computing processing system for use in association with the embodiments, by way of non-limiting example, is capable of executing software, such as an operating system (OS), applications/apps, user interfaces, and/or one or more other computing algorithms, such as the algorithms, modules, decisions, models, programs and sub-programs discussed herein. The operation of the exemplary processing system is controlled primarily by non-transitory computer readable instructions/code, such as instructions stored in a computer readable storage medium, such as hard disk drive (HDD), optical disk, solid state drive, Random Access Memory (RAM), a flash memory, or the like. Such instructions may be executed within the central processing unit (CPU) to cause the system to perform the disclosed operations. In many known computer servers, workstations, mobile devices, personal computers, and the like, the CPU is implemented in an integrated circuit called a processor.

It is further appreciated that, although the exemplary processing system may comprise a single CPU, such description is merely illustrative, as each processing system discussed herein throughout may comprise a plurality of CPUs. As such, the disclosed systems may also exploit the resources of remote CPUs through a communications network or some other data communications means.

In operation, CPU fetches, decodes, and executes the instructions from the computer readable storage medium. Information, such as the computer instructions and other computer readable data, is transferred between components of the computing system via the system's main data-transfer path.

In addition, the processing system may contain a peripheral communications controller and bus, which is responsible for communicating instructions from CPU to, and/or receiving data from, peripherals as discussed herein throughout. An example of a peripheral bus is the Peripheral Component Interconnect (PCI) bus that is well known in the pertinent art.

An operator display/user interface (UI)/graphical user interface (GUI) may be used to display visual output and/or presentation data generated by or at the request of processing system, such as responsive to operation of the aforementioned computing programs/applications. Such visual output may include text, graphics, animated graphics, and/or video, for example. Similarly, audio output may be provided.

Further, the processing system may contain a network adapter which may be used to couple to an external communication network, which may include or provide access to the Internet, an intranet, an extranet, or the like, such as the "cloud". The communications network may provide access for processing system with means of communicating and transferring software and information electronically. Network adaptor may communicate to and from the network using any available wired or wireless technologies. Such technologies may include, by way of non-limiting example, cellular, Wi-Fi, Bluetooth, infrared, or the like.

The disclosure is and includes a mobile device, components thereof, an operating system(s) thereof, and applications associated therewith, dedicated to behavioral predictions and mental, emotional, and physical health of the user of the mobile device. The operating system(s) of the mobile device use(s) feedback from the user in order to learn the user, and to address, remedy, change, or support the behaviors of the user.

Although the disclosed device, components, and software may include artificial intelligence (AI) features, those AI features are used solely to contribute to the learning models implemented by the device and its software, and to enhance the well-being of the user. That is, the device disclosed herein and its software provide novel aspects unknown in the prior art, and AI may simply contribute to, rather than forming the basis of, these novel features.

Simply put, in the prior art AI is generally trained and/or controlled by a third party's perception of reality. In the disclosed examples, although in some cases the AI and the learning features may include and/or be trained from external models, and/or have access to external data or libraries, in principal the AI and learning features may be "trained" solely or principally from the baseline of the user's reality, rather than a third-party's perception of reality, i.e., a third party's perception of right and wrong, or good or bad.

As mentioned above, all mobile devices provide significant and unused processing capabilities and data reception and accrual. Indeed, by way of non-limiting example, the iPhone includes at least 40 sensors of various types, the use of which is currently very limited. Further, the logic of current mobile device processing, as well as of mobile device operating systems, is provided by programmers, and the hooks into the device and sensor data of the application programming interface (API) are also exposed by programmers.

It goes without saying that the data deemed "important", and thus the data and data hooks exposed by programmers in the API as well as that relied upon by the device's operating system, would differ significantly if that exposure was provided by persons experienced with human health and well-being, such as psychologists, rather than programmers. Thus, a novel operating system (OS) of the embodiments, i.e., the personal functions operating system (PFOS) discussed throughout, is focused on exposing and using data and data hooks relevant to human well-being. Further, the disclosed personal functions OS may, at least in some embodiments, run on a processor discrete from that which runs the mobile device functionality; this discrete processor is herein referred to as the personal functions processor.

Thus, and as illustrated in FIG. 1, in some examples, the disclosure includes a mobile device 100 having a dual processor system, with the two processors in a master-slave relationship. The slave processor 130 is the mobile device functionality processor, as is known in the current art. The mobile device processor may also have accessible to it its own computing memory 132. The mobile device processor may handle mobile device functions, including external communications 134, control of and interface with the device's sensors 136, apps 138 and app management, etc.

Further, the mobile device processor has an OS 140 capable of operating the mobile device 100 and its various interfaces (e.g., GUI 142) and peripherals.

The master processor 110 is the personal functions processor. It may or may not have its own computing memory 112 associated with it, i.e., it may use the memory 132 of the mobile device CPU, albeit by encoding its data such that the data is inaccessible in any way to the mobile CPU; and it may or may not have its own dedicated apps 118 running in conjunction with it; and it has its own dedicated personal functions OS 120. Of note, the apps run by the personal functions OS 120 of the personal functions processor may sit hierarchically "above" the apps 138 of the mobile device operating system in the device stack (i.e., the operational and software layers)—that is, the personal function apps 118, and by association the personal functions OS 120, may be configured to hierarchically monitor and/or control the mobile device apps 138, in some or all circumstances, although the converse is never true, i.e., the personal function OS 120 and personal functions apps 118 are never subject to monitoring or control by the mobile device OS 140 and processor. Further, the personal functions OS 120 may be open source, and may provide an API 122 that exposes all data hooks relevant to human well-being, whether those data hooks stem from data provided by operation of the mobile device functions processor or of the personal functions processor.

Moreover, as the personal functions processor is the master processor 110, it may monitor and/or control any aspects, including the mobile device processor, the mobile device OS 140, the mobile device processor's electronics and sensors 136, the mobile device apps 138, the mobile device's memory 132, and the mobile device's communications 134. However, and as mentioned above, this monitoring and control is a one-way connection in the examples herein, at least in that the slave processor 130 has no ability to monitor or control any aspects of the personal functions processor or the personal functions OS 120, and no aspects of the personal functions processor, the personal functions OS 120, or the personal functions apps 118 are ever exposed to outbound data flow to the mobile device processor and/or OS 140.

Although various configurations of master/slave processor relationships are disclosed herein, it should be appreciated that sensors 136 may be configured to be physically accessible to any disclosed processor (e.g., master processor 110 and/or slave processor 130) and receive sensor data (e.g., biometrics) directly and/or indirectly. Further, sensor data received to any disclosed processor may further comprise any inputs from peripheral input devices (e.g., keyboards, mice, touch screen). In some embodiments, sensors 136 provide a direct biosensor feed into master processor 110 without the consent of slave processor 130.

Of course, it may also be the case that the slave processor 130 cedes certain functionality and control typical of a mobile device processor to the master processor 110. That is, the master processor 110 may assume direct control, to the exclusion of the slave processor 130, of one or more of: general on-chip sensing; camera; microphone; accelerometer; gyroscope; magnetometer; temperature sensing; proximity; LIDAR; barometer; GPS; ECG; fingerprinting; humidity; light; linear motion; position sensors; rotation vector; and/or environmental sensors. Even in such cases, the master processor 110 may remain isolated from external communications. As such, all communication band interactions and controls, including but not limited to WiFi, BT, cellular, and TCP, may remain the sole purview of the slave processor 130.

Further, the slave processor 130 may thus be any type of processor that typically serves a master role, but is enslaved to the master processor 110 in the disclosed embodiments. That is, all devices operating independently in the modern world may be enslaved to the disclosed master processor 110. Accordingly, the embodiments may allow for registration of beacon, or satellite, devices, which may be local or remote, and which may be enslaved to a master processor 110. Satellite devices may be mobile or non-mobile, and may include, without limitation, devices such as vehicle processors, appliance processors, television processors, radio processors, and the like. As such, the master processor 110 may be co-located with the user, such as at the user's home, for the sake of physical security of the master processor 110, and/or may be located in the cloud on a remote server or distributed remote servers, for the sake of enhanced data security of the master processor 110.

As such, the dual processor, master-slave configuration of the embodiments may mimic the right and left hemisphere operation of the human brain, with left hemispheric control, thus significantly enhancing the ability of the disclosed system to improve privacy, anticipate human needs, expand self-knowledge, and support human well-being. That is, in the human brain, the left hemisphere is largely responsible for emotional state and feeling—which is mimicked by the personal functions processor in the disclosed system—and the right hemisphere is largely responsible for logic and mechanical aspects of thinking—which is mimicked by the mobile device processor in the disclosed system.

Further, the master-slave arrangement, with the "left brain" of well-being serving as the master, ensures that the mobile device processor/OS and/or the beacon/satellite slave processor 130 and/or OS 140 (also referred to herein collectively as the mobile device processor/OS) can never harm the user, or even try to scam the user or sell to or upsell the user in a manner detrimental to the user. This is because such "behaviors" of the classical mobile device OS and its apps may be blocked by the disclosed personal functions OS.

Accordingly, the personal functions OS is, in essence, operating as the interface and gatekeeper of the master and slave processors (and the slave OS). The personal functions OS/master-slave interface provides connectivity, either directly or indirectly, the various functionality under the purview of the mobile device processor/OS, including sensors, mobile device apps, external communications, and the GUI. The personal functions OS also performs the learning and pattern recognitions discussed throughout, including any comparisons needed to make any comparisons in the course of pattern recognition, and builds the disclosed wholistic virtual avatar in accordance with the pattern recognitions, and performs all of the foregoing functionality while keeping all data involved safe and secure, outside of any visibility to the mobile device processor/OS as well as anyone who is not the established user/owner of the device.

Moreover, because ones of the embodiments allow only one way communication from the master to the slave, harm, selling, upselling, or scamming may be blocked by, or at the direction of, the personal functions OS, particularly because the mobile device processor/OS is never allowed to "learn" the user or her preferences as it does in known mobile devices, such as through the use of cookies and tracking.

That is, only the personal functions processor/OS has access to any data involved with the wholistic personal avatar associated with the device.

In the current economy as it relates to mobile devices, the mobile device provider is a gatekeeper for apps provided using the mobile device provider's chosen data hooks exposed in its controlled API. This is the case for two main reasons: first, so that the mobile device provider can control the app environment in a "one size fits all" community; and second, so that the mobile device provider can profit from offerings in the app environment that it provides.

This app environment, in which mobile device providers serve as the middle-man, limits the economic viability of alternative app-driven financial models, and practically eliminates the desirability of the presence of any apps not leading to money, power, and success for the app provider. That is, the known app financial model is very uniform—the user pays for an app or occurrences in-app, and the revenue therefrom is shared between the app-store provider, i.e., the mobile device provider, and the app provider.

Figure 2:
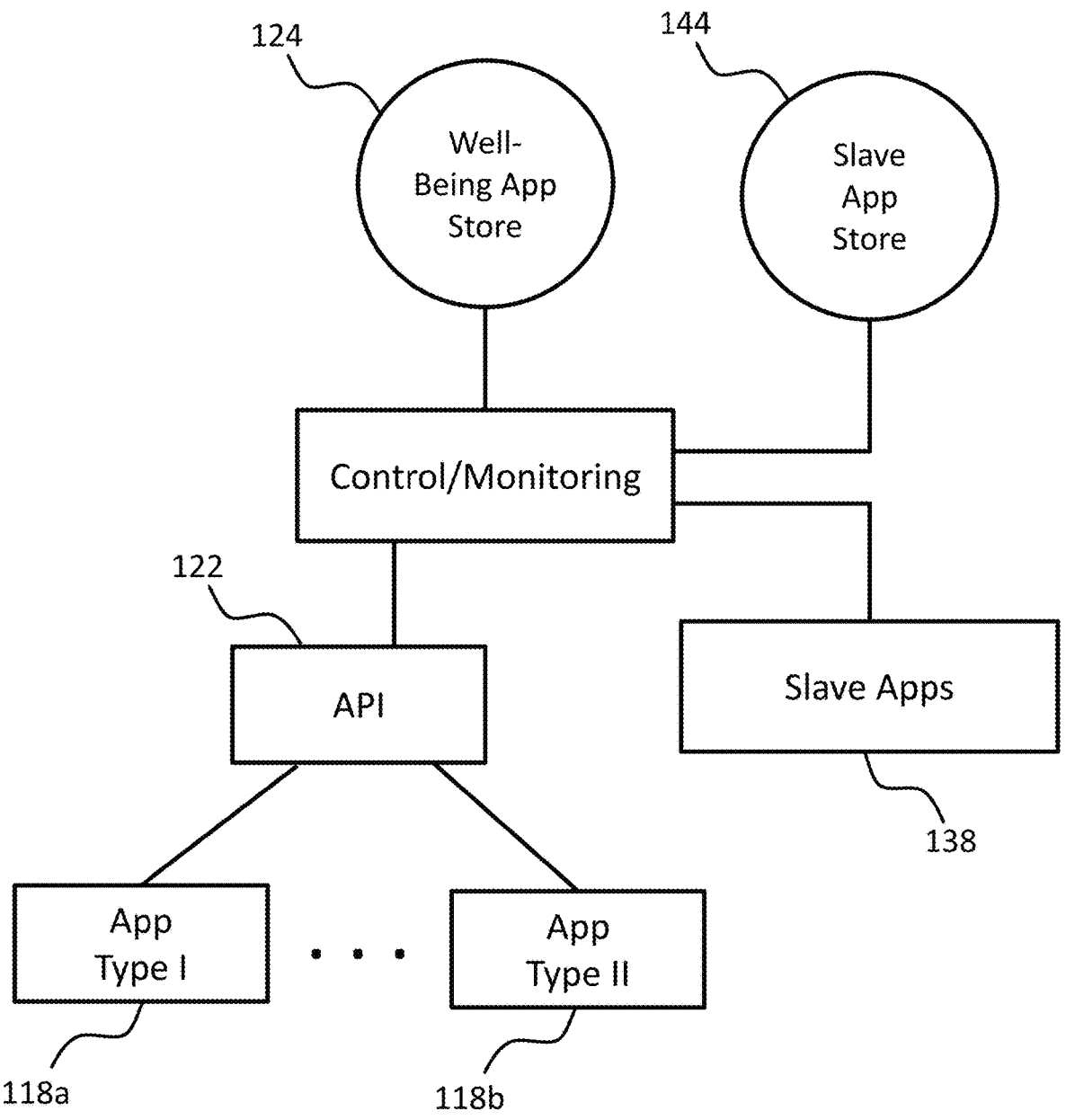
FIG. 2 graphically depicts aspects of the disclosure.

In a very contrary manner to the foregoing, the embodiments may provide a unique "app store" with unlimited available financial models, in conjunctions with apps available from know app stores (resident in association with the mobile device processor/OS, but controlled by the personal functions OS). By way of example, a user may, because of the destructured relationship between user, device provider, and app provider herein, gain shares, discounts, credits, coupons, or the like from an app the more said app is used. Further, the differing levels of control by the mobile device provider, and the limited involvement thereof in financial transactions, may effectuate differences in financial models. For example, well-known apps that follow the known typical financial model may receive one level of treatment by the app environment provided in conjunction with the personal functions OS, such as by receiving access to only certain data hooks from the API 122; however, other apps or app types (e.g., App Type I 118a, App Type II 118b) with a focus limited to an aspect of human well-being may receive a different level of control, financial access, and/or access to a more expansive set of data hooks. This relationship variability for the API 122, data hooks, and the app store is illustrated in FIG. 2. Further, this additional app-store (e.g., well-being app store 124) may be provided in conjunction with the known app store (e.g., slave app store 144) provided along with the mobile device OS by the mobile device processor.

Simply put, the current large number of sensors in all mobile devices is capable of exposing significant data regarding human identity, psychology, sociability and well-being. For example, the voice patterns of each person are unique, i.e., word structure, volume, tonality, etc., in correspondence to that person's current state. Further, the user's volume and tonality is available at all times to the phone's sensors, such as the microphone(s), and each aspect of the user's voice has a unique indication specifically for that user, which the personal functions OS may learn over time by monitoring that user. For example, an increase in volume of a certain percent, with a tonality change of a different percent, may indicate excitement for one user, but may indicate anger for another.

Likewise, a front-facing sensor or lens may "see" a user at all times when she is viewing the mobile device's screen. Thus, the sensor or lens may "see" the user's facial expressions, each aspect of which may have specific meaning particularly for that user, which the personal functions OS may learn over time. Likewise, the master processor 110 may monitor the device's screen to "watch" what is on it, and may do so passively and without interaction with the slave processor 130.

Similarly, the way a user carries her phone, picks it up, puts it down, puts it away, and takes it out, are all readily sensed by current mobile devices. Variations in all of these actions are also highly indicative of the current physical and emotional health and mental state of the user, and this high level of indications varies significantly for each user, and may be learned for the particular user/owner by the personal functions OS of that particular device.

Yet further, the phone includes numerous sensors capable of performing bio-sensing and pattern sensing which is, of course, highly indicative of: the presence of a person; the identity of the person present; and the ongoing physical health and mental state of the person. This assessment is done in the embodiments in a manner that differs for each user, based on learnings about that particular user. As such, the embodiments may enable contextualized human identification and security based on each unique use case. By way of example, the device may thus have a different identification to access the device as compared to logging in to a social media app—that is, the identification of a person, or a specific person, may be varied in the embodiments based on the necessary degree of confidence for the use case requested. Obviously, a higher degree of confidence in identification is needed for the most private or intimate apps than for a fantasy sports app. Likewise, some apps may necessitate certain identifications, such as, for example, a gambling app, which may be required to identify the user is he/she who can properly access funds, is 21 years old, and is a resident of or is present in a certain state or states.

As such, the embodiments may provide confirmation of a true-human capable of sensed interactions indicative of mental, emotional and physical health that should be monitored, and further may enable unique identification, without logging in, of that human, which identification brings with it, the true-human data of the person in the form of his/her personal avatar. As such, pursuant to instruction from the master processor, all profile data is consistently loaded to the personal avatar, and that personal avatar is consistently exchanged with the slave processor 130, OS 140, and/or devices.

Consequently, slave devices, apps, and the like will behave in a manner according to the actions, emotions, and preferences of the personal avatar. In an example, a vehicle processor may act as a satellite/slave to the master processor 110 on a mobile device. Thus, as the user drives, eye movements, stress levels, driving preferences, and driving habits may be tracked, and this "driving package" may be transported, such as to other vehicles or to self-driving vehicles, along with the user's mobile device. In such a case, any vehicle will then cater its settings to that individual user, and a self-driving car will drive just as the user would. Similarly, the driving package app will recognize variations in the user, such as if the user is drunk or sleepy, based on differences perceived in the user's driving actions, reaction times, and so on.

Yet further, the user's preferred driving experience may be used, for example, by other apps. For example, an app for ordering an Uber, a Lyft, or a cab may not simply find a driver for the user upon request, but may find the "right" driver for that user, i.e., a driver with similar driving habits to those preferred by the user, a driver with vehicle settings, such as temperature and lighting, akin to those preferred by the user, and so on.

Additionally, the user's use of and manner of interaction with the device are also readily available to the personal function OS by extraction from the use of the mobile device processor/OS, and are highly indicative of the user's well-being. That is, the apps viewed, content viewed, searches performed, responses to texts or emails generated, and the viewing time for some or all of the foregoing, may contribute to an assessment of the user's well-being.

This is highly contrary to the known art, in which the data from the hardware/firmware layer of a stack is used by apps in the app layer not to help or inform the user, but instead to sell to the user and/or manipulate the user. As such, the personal functions OS may have override capability for this tendency of apps operating in the app layer within the mobile device functions layer.

Accordingly, the personal functions processor performs continuous mental-health and well-being pattern recognition. That is, within parameters set or agreed to by the mobile device user, the personal functions OS may continuously monitor the user, principally using all sensor and data inputs under the control of the mobile device processor and having data incurred by the mobile device OS, in order to track emotion, health, and mental state.

Moreover, all of the foregoing functionality may be provided simultaneously by the dual processor and dual OS system discussed herein. That is, the device may identify a presence of a person, may uniquely identify the person, may assess the well-being of the person, and may perform a task, such as an app-opening or in-app task, all simultaneously.

Figure 3:
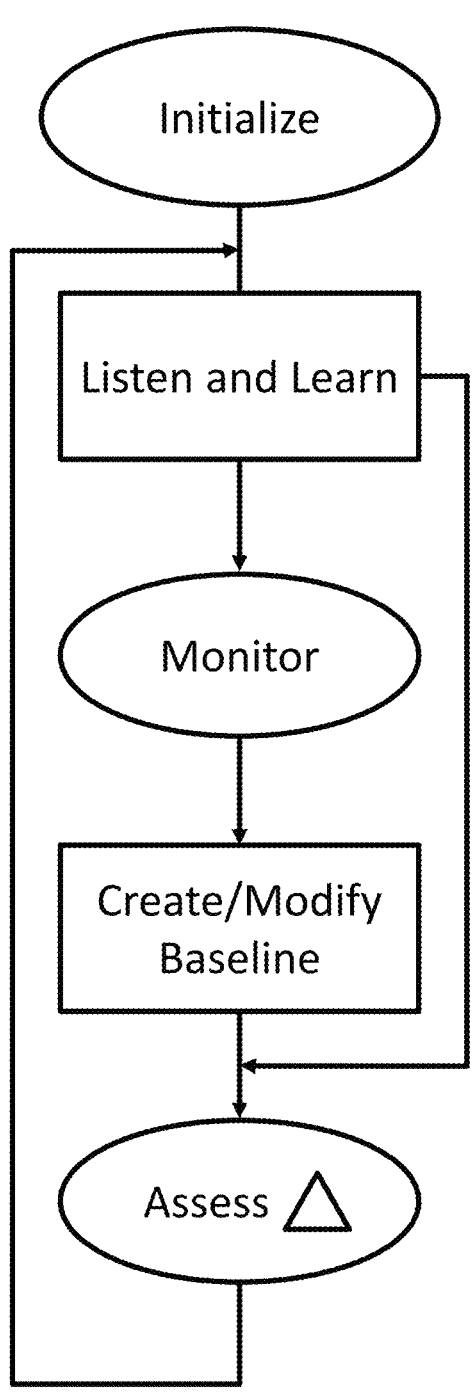
FIG. 3 graphically depicts aspects of the disclosure.

As illustrated in FIG. 3, the initial use of the mobile device may comprise a listen and learn mode. That is, the personal functions OS may monitor the incoming data to the mobile device OS to get a baseline of the user in all areas of significance, such as areas that illustrate physical, emotional and mental health, including the user's typical, unfettered use of the mobile device and her physical, emotional and mental reaction to that typical use. Uniquely, this listen and learn mode may allow and monitor the use of any or all known apps typically in use on mobile devices, i.e., the mobile device apps of the mobile device OS.

Therefrom, the personal functions processor may "see" and/or record all data, and the reactions to all occurrences by a user, to form the baseline profile. Simply put, the baseline is the user's wholistic digital/virtual personal avatar, possessing all physical, mental, and emotional characteristics of the user, at least at baseline, when the mobile device is first associated with that user. The baseline, for example, may be the user's average condition, the user's most frequent condition, and so on as will be apparent to the skilled artisan in light of the discussion herein.

As part of the baseline development, variability, i.e., a delta, is sensed, and corresponded to occurrences that are sensed as possibly causing the variations. In short, the most consistent conditions may be deemed the baseline, as indicated above, and the variations are presumed to be the deltas from the baseline.

Thereafter, the deltas are quantified and corresponded to the occurrences during which the deltas happen. As such, a feedback loop is developed, in which: the baseline is assessed; occurrences that lead to deltas from the baseline, and the amount of effect from baseline (i.e., how positive or negative the variation from baseline is, from a well-being perspective) for each delta occurrence, are assessed; and modifications to baseline, and as well as delta responses from the baseline, are constantly reassessed over time as changes in well-being are sensed.

Figure 4:
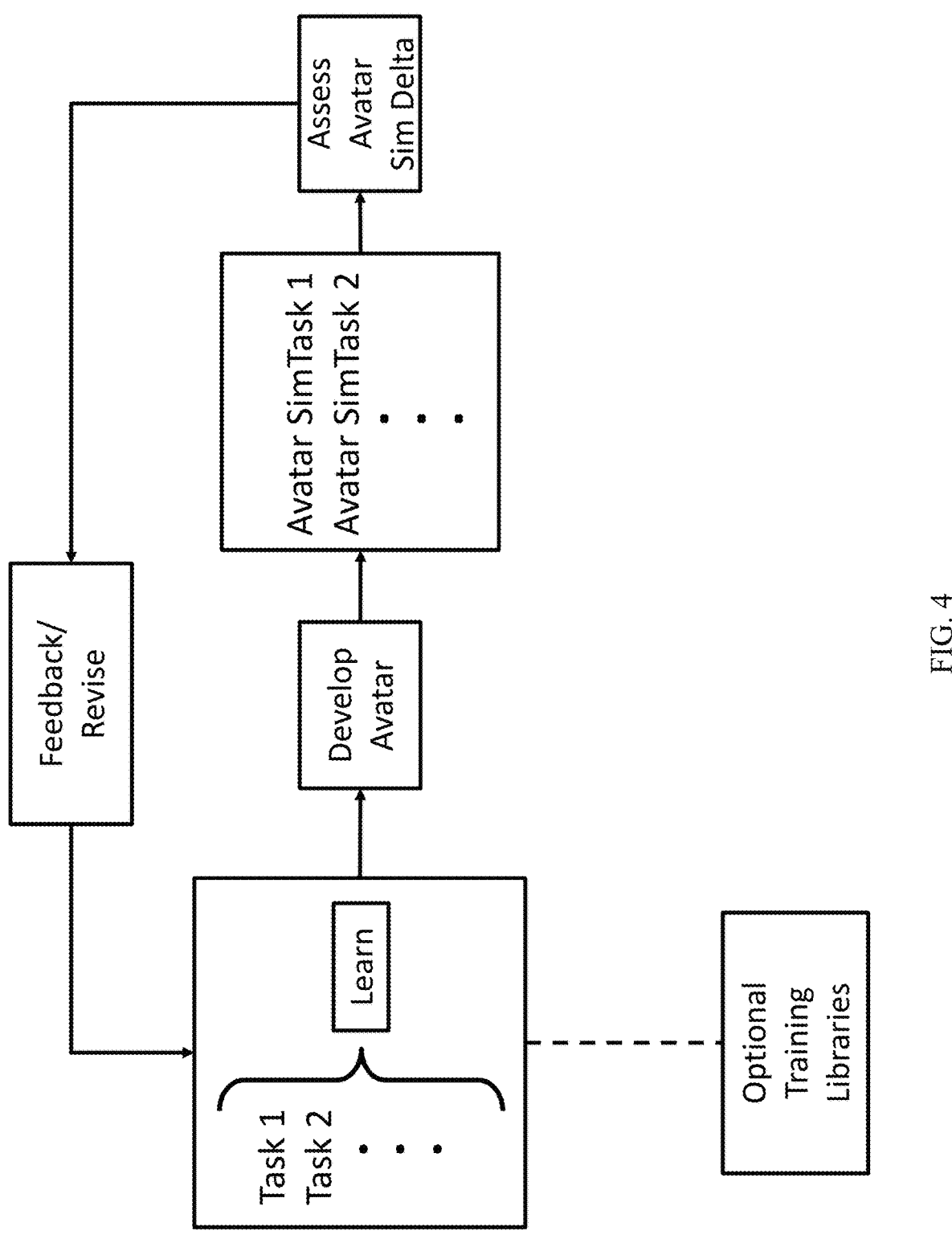
FIG. 4 graphically depicts aspects of the disclosure.

The foregoing may occur using the detailed feedback system in FIG. 4. Of note, this system is a closed loop, and thus maintains all data obtained in any portion of the loop as safe and secure by the personal functions OS that is performing that data accumulation loop. In this system, the personal function OS may or may not have access to outside models and/or training modules, i.e., libraries or models, to assess "good", "bad", "healthy", "unhealthy", etc., which is contrary to the known art (which requires training). Further, any such access may be made through the mobile device processor/OS at the direction of, and solely for the knowledge gained by, the personal functions OS.

Whether the personal functions OS does or does not use outside training or access libraries for learning, the personal function OS may then engage in avatar projection/simulation and unsupervised learning, both to create the baseline initially, and then to vary it based on the deltas/feedback. That is, the personal physical, mental and emotional avatar is developed via the process above; the personal function OS then uses the avatar to project behaviors via pattern recognitions—likely, good, bad, etc. The personal function OS may then monitor the mobile device OS to see what the mobile device processor is actually asked to do; and the simulation that is forming the wholistic personal avatar model is then changed, as and if needed.

Once the avatar is fully developed, and delta occurrences are noted (including delta degree), attempts may be made by the personal function OS to modify information provided by the mobile device OS, and/or to modify the use of the mobile device OS, to improve the user's well-being. Simply put, the behavioral model upon which the disclosed system is trained to eventually start aiding in improving the user's privacy, self-knowledge and well-being is the monitoring of the user herself from first use. That is, the assessed increment or decrement in the user's physical, mental, and emotional well-being is assessed versus the user herself. Ultimately, the user trains the mobile device to think and act like the user when the user is in a normal/good state, so that the mobile device realizes when the user is not in a good state and can endeavor to return her to a good state using the things that the mobile device already knows improves the user's state.

As mentioned, the personal function OS may access a plurality of mobile-integrated or remote libraries to aid in learning, particularly to gain relational correspondence. For example, the mobile device can use a library to assess a user's race, i.e., a library of known persons of certain races may be compared against images taken by the front facing camera. Likewise, a library of tiers of income versus typical amount and frequency of purchases, when compared against user purchase activity on the mobile device, allows for an assessment of socio-economic position of the user. Yet further, an assessment, using mobile device sensors, of a user's BMI, when viewed in light of a comparative library of levels of heart rate and blood pressure (also assessed via mobile device sensors) for certain BMI, may indicate certain cardiac conditions.

Accordingly, particularly in listen and learn mode, the personal functions OS may engage in a wide variety of activities to assess the avatar's characteristics, and to gain feedback. For example, if the mobile device sensors indicate, such as via GPS, that the user is in a Catholic church, and the microphone of the mobile device senses the user is singing, and the accelerometer and gyro sensors of the mobile device sense that the user is standing, sitting, and kneeling in succession, the personal function OS may cause the mobile device GUI to ask "Hi [User], just wondering— are you Catholic?"

Once the baseline and deltas are assessed, and at least an initial avatar profile completed, the personal functions OS may make assessments using sensors of a user's condition, and may "know" how to adjust the condition. For example, based on mobile device sensing of breathing and eye movement, the personal functions OS may assess that relaxation, focus, or mindfulness is needed to put the user in an increased state of well-being, such as to get the user in a mindset to give a speech noted in the mobile device calendar, or for any other of a number of known or unknown circumstances, for example.

The personal functions OS may then know precisely how to get the user into an enhanced state of relaxation, focus, better breathing, mindfulness or even positive flow states, based on the developed avatar and pattern recognitions. By way of example, the disclosed system may understand that music (or a certain song or certain type of music), a video (or a certain movie or a category of video), or a certain AR experience is highly likely to move the user's well-being into or closer to the desired state. And, of course, if the experience is provided and the expected result does not occur, that feedback is used in the future to modify the approach the next time such a change in the state of well-being is desired or needed.

Finally, of course, although the user may also ask the mobile device for a certain experience to relax her in the known art, this needn't be the case in the disclosed system. That is, the personal functions OS "knows" the correct experience to provide to the user when she needs to relax, and can simply provide the experience without the user asking for the experience, which is unheard of in the known art. Needless to say, the mobile device may be instructed by the personal functions OS to provide data whether the user is in an appropriate position to receive the selected experience.

Of note, the foregoing may also be operable for a single multi-party device. In such a case, a wholistic avatar may be developed for each user, and the device may provide the information and experiences only for the user then known by the device to be in possession of the device.

Some or all of the behavior modification and/or suggestions to enhance well-being may be at the option of the user. For example, although an external library/model may suggest that base jumping is a very poor choice for physical well-being, the personal functions OS may also recognize that the user's maximum joy, emotional refresh, and sense of exhilaration is optimal while the user is base jumping. As such, if the user wishes to maximize her emotional health over all else, the disclosed system may not recommend against base jumping due to the user's selected options. Relatedly, if the personal functions OS does recognize that base jumping is physically dangerous, it may try to progressively "correct" the dangerous behavior, such as by finding, through sensing, AI research, and/or the use of external libraries/models on comparable experiences, other behaviors that have, alone or in combination, a similar positive emotional effect on this particular user, but which are far less dangerous than base jumping.

The foregoing allows the system to uniquely and particularly offer solely to the verified user, "personal feedback", "digital reflection", or "your data trends" so as to help improve that specific user with his/her symptoms, retard the progression of physical or mental conditions, help the user seek medical attention, or so as to simply alert the user of physical or mental changes.

But the benefits may go beyond mental and behavioral health assessment-personalized data sets may help provide to the user highly customized self-knowledge, and relevant content, education, tailored entertainment, unique advice, tutoring, or even the ability to improve human behavior, focus, attention, mindfulness and flow states. Biometrics in combination with tracking digital activity on the mobile device (email, text, social media, etc.), enables a unique and safe "learning system" that learns the user. Uniquely knowing the user, perhaps better than the user knows him/herself, allows for: automated content management based on the user's age, gender, location, cultural preferences, mental and physical state; a misinformation/disinformation engine to ensure good quality data is presented, and falsehoods or SPAM are note; periodic, such as daily, mood assessment; periodic, such as daily, mental health assessment; focus, attention, and mindfulness, including breathing tracking and improvement; and/or Socratic reflection for better self-knowing and self-improvement.

By providing a true, tailored, near-ideal "digital companion", which is safe, secure, non-addictive and alleviates feelings of chronic loneliness, the current loneliness epidemic worldwide is addressed. Accordingly, the embodiments can address depression, suicidal ideation, and so on.

Similarly, as mentioned herein, in some embodiments the device's avatar learning, i.e., the learning of the "digital companion", is solely based on its exposure to the user from first use, the development of a baseline, an assessment of deltas, and received feedback. In such a case, the personal functions OS may have no sense of "good" or "bad", "dangerous" or "safe", and thus may solely recognize that, when engaged in this certain behavior, the user remains physically unharmed and experiences optimal emotional and mental health. Therefore, in this case where no external training of the personal functions OS occurs, the mobile device may do nothing whatsoever to recommend against base-jumping in the foregoing example.

In the known art, the providing of artificial intelligence (AI) on or by a mobile device is not necessarily aligned at all with the good of the user. Rather, the AI provided in the known art typically aligns with granting the user's wishes, and enhancing the success, wealth and power of one of the user, an app provider, or the mobile device provider. This, of course, contributes nothing to the user's overall physical, mental and emotional well-being which, as referenced above, is often disconnected from even the case where the AI supports the user's success, wealth, or power.

On the contrary, the disclosed system provides an AI that supports overall well-being through the personal avatar development. To that end, the AI of the disclosed system may allow for not only one way, i.e., user requests to AI, but also two-way communication. Further, the AI may select the premium modes of communication, based on its learning in the development of the overall personal avatar, to obtain optimal adoption by the user of its learning and/or suggestions to improve the user's well-being. Current psychological research indicates that the optimal "convincing" modes of communication for most users are voice or video, but, as indicated throughout, the personal functions OS may learn differently on a user-by-user basis.

All of the foregoing, including the learning to develop the physical, mental and emotional personal avatar, and the capability to control mobile device access/login from the personal functions processor/OS, rather than the mobile device processor/OS, makes the disclosed system extraordinarily more safe and secure than known devices. First and foremost, because the personal functions OS builds a wholistic personal avatar, it has a great deal more information regarding the user/owner than ever occurs in prior art mobile devices.

Figure 5:
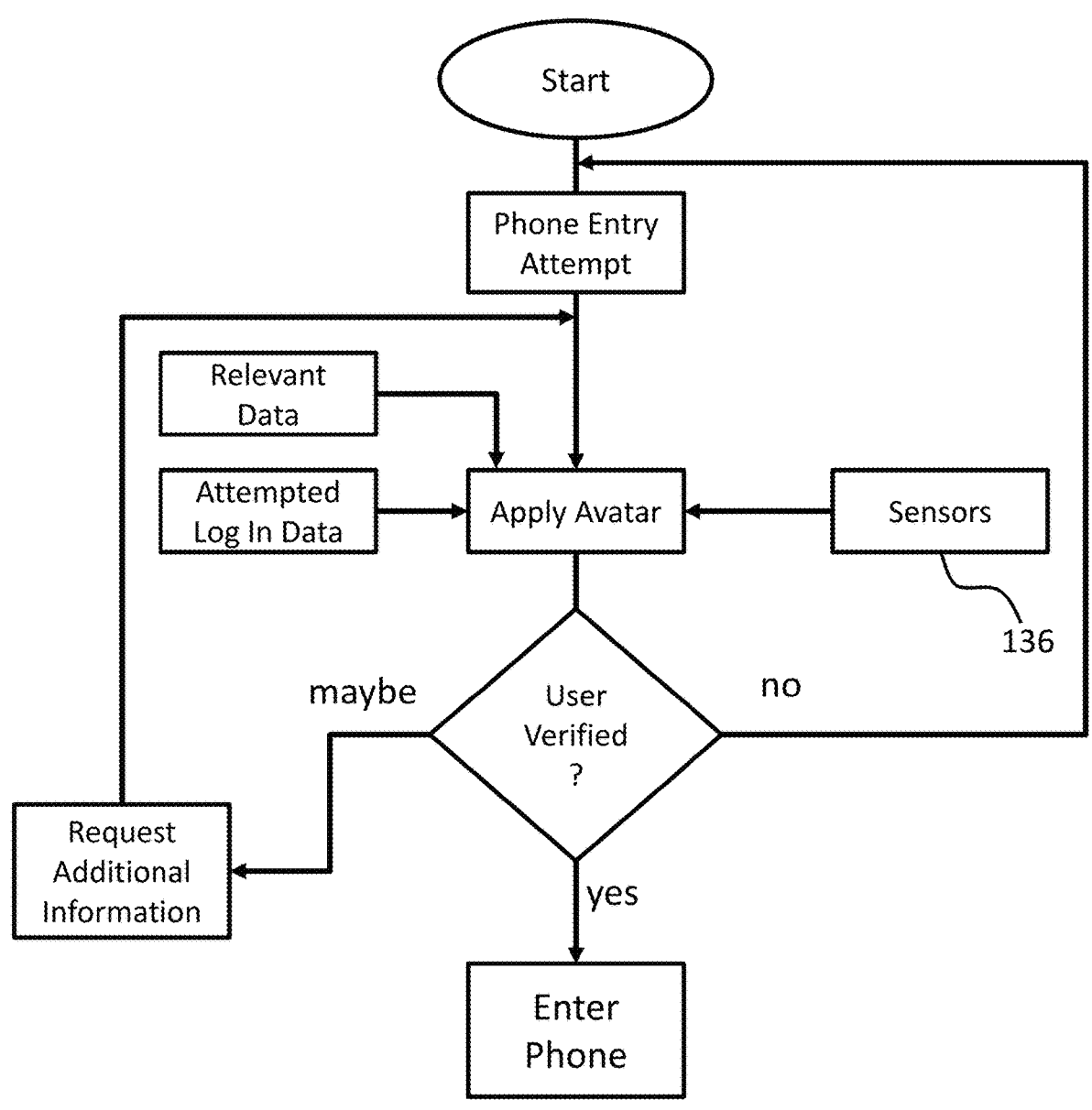
FIG. 5 graphically depicts aspects of the disclosure.

Because of the foregoing, "logging in", in the known sense, may become a thing of the past, as is shown in FIG. 5. That is, the recognition by the disclosed mobile device that an attempted access is from the correct user/owner is wholistic, rather than by limited entry of one or two of a password, pass code, facial scan, or finger print, as is the case in the known art. Simply put, because the disclosed mobile device system "knows" the user via the development of the personal avatar, it knows the user across biometrics, i.e., it knows a user's face, eyes, voice, gait, height, phone grip technique, locations, moods, hand pressures, breathing patterns, resting heart rate, etc., and thus can wholistically use these factors to "log-in"/recognize the user. This means that the disclosed mobile device cannot be "duped", tapped, or otherwise violated, and thereby no aspects available to the true user can be opened by anyone other than the owner/user (and any administrators who oversee the user/owner, such as a parent), such as if the phone is lost or stolen.

An ongoing chain of custody of the mobile device can be initiated and maintained using the constant and contextualized authentication of the user by various sensors as described in [0093].

For example, the phone may simply log-in the user when the phone is taken out of a user's pocket while walking, and the overall person matches one or a series of aspects of the wholistic personal avatar. If there is any question, the mobile device may ask the user to speak; may ask the user her religion; may ask the user where she ate dinner last night; may ask the user where she went to college; may ask the user to shake her phone with her right hand; or may ask the user her mom's name, by way of non-limiting example, until the device becomes "convinced" that the user is (or is not) the correct user/owner.

Moreover, biometric interactions allow for a variety of user interfacing and external device connectivity. By way of example, the system's comprehension of vision/eye characteristics may allow for interfacing with smart eye glasses, AR/VR headsets, and so on, and may further allow for applications such as user authentication, full self-driving, and eye-based gesture directives. Moreover, gesture sensing and/or directives may be uniquely assessed with regard to that specific user.

Eye tracking in augmented reality (AR) and virtual reality (VR) could pose significant privacy risks due to the amount of sensitive information it can collect. More particularly, eye tracking data is personally identifiable information because it can be used to identify individuals, individual's interests, and individual's thought processes. This data can be combined with other personal information to trace or fake someone's identity.

Yet more specifically, eye tracking specifically can collect a wide range of highly sensitive data. Such data may include: cognitive states, in which eye tracking reveals information about a person's mental state such as focusing, being attentive, or deep learning; personality traits, in which eye tracking reveals information about a person's personality and interests; demographics, in which eye tracking reveals information about a person's age, ethnicity, and drug usage; and emotions and fears, in which eye tracking reveals information about a person's emotions and fears.

The disclosed system thus uniquely enables the verified user identified by the wholistic personal avatar to exclusively use and exploit his/her own biometrics information, such as vision/eye tracking, without risking exposure of personally identifiable information to the internet or to another human. This individualized exploitation may include sole use by the user of particular external devices and/or novel applications, such as wearables (i.e., wristband, watch, smart ring, earphones, headphones, mobility devices (i.e., car, scooter, bike), or robotics (i.e., humanoid, appendages or extensions, service bots, or robo-pets).

Additionally, as the user is wholistically known to the device, it is known if the user is lying or under duress. Thus, the device would be aware if the user was being forced to open/log-into the device, and can consequently prevent log-in, or may block access to certain features or content upon log-in, when the device recognizes that the user is asking to log-in but doesn't really want to.

Yet further, use-safety and app-authentication may become a two way process in the disclosed system. As mentioned above, the device "knows" all aspects of the user, and hence can know (and/or be taught, such as via initially access to the libraries mentioned above, followed by the learning to build the wholistic avatar discussed throughout) what is safe for, desired by, or detrimental to the user.

For example, the disclosed device "knows" if the user is a child, and if there is a parent administrator, and so can filter content accordingly, without implementation by the parent of specific parental controls. Filtering, as discussed herein, may include blocking a request made to the UI, blocking the delivery of content already requested, blocking inbound information that was not requested, blocking inbound or outbound content of a certain type, category, or indication by a library, and so on. The personal functions OS can also limit downloads, as well as app or in-app purchases, and so on, without the typical hassle to the parent of having to set up parental controls or give case-by-case permissions.

Of course, numerous other safety and/or security features may be available via the disclosed system. For example, content may be fact-checked by the AI aspects, and all content that are 60% or more likely to be false may not be made available to the user. Likewise, the AI of the personal functions OS may remove all content having certain biases, all content having certain offensive material, all content making available purchases over a certain value, and so on. Yet further, the AI can spot bots, viruses, and deep fakes, and it knows all users within the closed universe of devices having developed personal avatars for their own respective users are real, and the content generated by their users is legitimate, and can thus indicate/verify/authenticate same to and from the universe of like-devices.

All of the foregoing features on safety, security, and verification are available in the embodiments due to the unique structure of the disclosed system. That is, the placement of the master processor and OS between the user and the slave processor and OS enables these features. Thereby, user-targeting, such as of advertising and marketing, and opt-ins and opt-outs for content, purchases, and the like, may still be allowed on the disclosed device, but may be overseen and controlled, to the benefit of the user's well-being, by the personal functions processor and OS. For example, a targeted ad for something of significant interest to the user may be provided, along with a 40% off coupon, by the personal functions processor and OS if, and only if, the user relaxes her breathing and lowers her heart rate by 10%, and the item of interest will not decrease the user's well-being.

Figure 6:
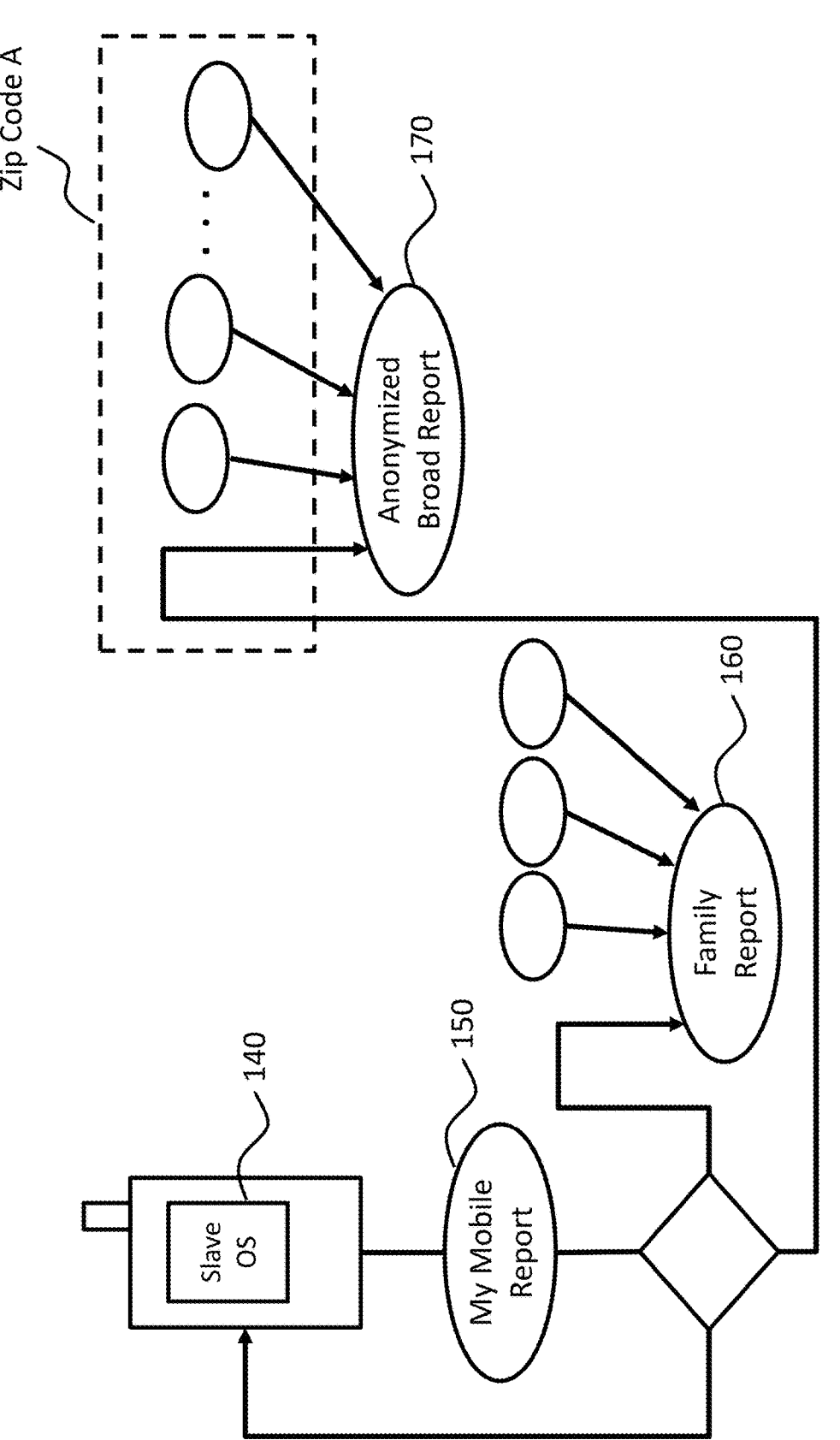
FIG. 6 graphically depicts aspects of the disclosure.

Needless to say, and as shown in FIG. 6, significant reporting may be made available from a single disclosed device (e.g., my mobile report 150), within "families" of the disclosed devices (e.g., family report 160), or anonymously across categories of devices (e.g., anonymized broad report 170). For example, a category may be zip code, and the disclosed embodiments may allow reporting of happiness, relaxation, physical fitness, or other levels such that these factors can be compared between populations by zip code.

Similarly, child-users may be reported to parents within a family group of the disclosed devices. Needless to say, child-user reports may or may not include what the child user is doing on her device, as may be done in the known art. But, more particularly and in distinction from the known art, the family of devices in the disclosure may report on how the child feels—i.e., is she anxious, sad, happy, excited, physically healthy, and what percentage of time, and to what extent, is she each of those things. Furthermore, the report may indicate what she is doing on the device when she's happy, or when she's sad.

Individual reporting may include all of the foregoing, i.e., what the user is doing, or not doing, that makes her happy, sad, lonely, excited, and so on. As such, the device's reporting may advise the user on how to move from a negative mental state to a normal one, or from a normal mental state to an enhanced one. Alternatively, such as with prior user permission, the device may simply begin to transition the user through mental states, based on its perception of its own internal reporting on the user's mental state.

Individual reporting may additionally include the physical reporting discussed throughout. By way of example, such as using access to outside "symptom" ones of the aforementioned libraries, the device may spot illness or disease, in some cases long before the user feels symptoms or receives a doctor's diagnosis. Additionally, the device may "probe" the user if it needs additional information to make a report, and or may make recommendations to the user to address possible health issues. For example, the disclosed device may aid in early detection of Parkinsons, dementia/Alzheimers, brain fog, depression, addiction, cardiac issues, the flu, and so on, and may further make recommendations, or otherwise lead the user, to take remedial action.

As such, the personal functions OS, the AI aspect thereof, and/or one or more personal functions apps may recognize something is wrong with the user. By way of non-limiting example, the user's stride length and stability may be sensed by the device to have changed in the last 3 months. The device may thus indicate to the user, "I noticed your sleeping patterns have changed, as have your stride length and stride stability, in the past 3 months—are you feeling OK?" Dependent upon the user's response, the device may probe further. For example, the device may ask the user, "OK, can you tell me more about how you are feeling lately? Are you eating differently?" Once again, based on ongoing interactions with the user, the personal functions OS/app may begin to suspect the user may be in the early stages of Parkinson's, when the disease is at its most treatable. The device may consequently say, "would you consider moving your arm up and down 5 times for me and walk 10 steps forwards and backwards" and monitor the motion/gait of hands and legs, or "would you consider seeing a neurologist in the near term? If so, I am happy to find a nearby appointment with a highly reputable neurologist that operates within your insured network of doctors."

Simply put, the disclosed device does not diagnose the user with Parkinson's—the device is not a doctor, and hence cannot make such a diagnosis. However, the wholistic personal avatar developed by the device allows the device to know when the user is no longer the same over a certain timeframe, and the device is able to use the manner of the changes and the timeframe of the changes to begin to formulate what might be affecting the user, and is then able to help the user best address the changes.

The disclosed device, system and method is thus "concerned" with the user, in mind and body, compared to herself. The device, system and method herein is also able to provide information, content, and action to get a user back to, and keep the user at or better, her own personal baseline of her wholistic personal avatar. For example, the device may provide exercises to improve mental, physical and emotional health. In short, the device may nudge the user to health, at which time the healthiest option for the user may be to put the device down, and, unlike the known art, the device accepts that outcome.

The device, system and method detailed herein gets to know the user, and allows for an economic arrangement that supports the user's well-being. The device may, for example, provide a gamification experience in a manner similar to older toys that interacted with the user and got to know the user in order to bring happiness. However, the disclosed embodiments are vastly superior to these known interactive toys, as they can discern nearly anything that will enhance the user's well-being, and can provide it. For example, some users may be assessed as to what they love the most, and then may be connected to an AI-driven VR experience that provides that to them.

In another example, the device may periodically provide simple micro-content to slowly changes the user's physical or mental state over time. Of course, the user may then make micro-payments for this micro-content. In an alternative financial arrangement, developers developing personal functions apps, as well as the users of those apps/device owners, may receive shares in the mobile device provider over time, such as due to ratings supporting the goal of well-being, such as for loyalty over time, and so on.

As such, the disclosed personal functions processor and OS, and the AI component thereof, needn't be trained, although they may or may not have access to the external libraries, such as via the cloud, as discussed throughout. Rather, the training is simply learning from the user about the user, including by tracking the user. Information tracked may include, but is not limited to: bio-sensed inputs; visual/audio inputs; electronic activity/content accessed/apps used; GPS location; weather; and so on.

More particularly and as discussed throughout, the stack executed by the master processor 110 may not only include access to bio-sensing/biometrics provided by the phone hardware from the slave processor 130, but may additionally include biometric safety and security and AI, and specifically AI security services, as referenced throughout, and also philosophical and psychological safety and security.

That is, the biometric sensing controlled by the slave processor at the direction of the master processor 110 may safely and securely capture a user's face, eyes, palm, hand, handprint, finger, fingerprint, feet, footprint, skin, skin color, voice, speech, breathing, walking, and/or motion as unique biometrics. Also sensed may be environmental conditions, location, surroundings, and other personal features like resting heart rate, heart rate variability, skin temperature, blood oxygen saturation level, and exercise and sleep cycles.

The device, system and method detailed herein may measure, track and/or predict one or more user's well-being and/or health. Generally, a user's well-being and/or health may include any of environmental, physical, occupational, mental, behavioral, psychological, emotional, intellectual, spiritual, financial, and social well-being and/or health. Well-being information of a user may be captured by the disclosed sensors, or entered in the form of a well-being assessment, such as behavioral psychology evaluation, or a mental health examination performed by a professional. To capture a wholistic view of a user's state, the device, system and method may measure or track any known environmental parameters and biometrics, for example including, but not limited to, a user's exposure to chemicals and/or plastics, a user's air quality, a user's water quality and hydration, a user's exposure to sunlight, a user's diet and eating habits, a user's medications and health plan, a user's sleep schedule and sleep habits, a user's movement and exercise habits.

Accordingly, in addition to aspects of the user's physical well-being, the foregoing and other information tracked allows for the device to assess the baseline emotional state, and variations therefrom. The physical, mental and emotional states may be assessed as normal (based on proximity to baseline across a number of sub-categories), negative/unhealthy (as compared to baseline), and positive/very healthy.

The user may allow, via interaction with the master processor, the system to autonomously collect the aforementioned and other biometrics always, or only for a given period of time, to build this "baseline" and to use it for an authentication, safety and security and/or privacy model. Of course, the system may be pre-programmed with what data is needed for each biometric channel to be at a suitable level for verification and validation, either based solely on that biometric channel or based on that channel in combination with one or more other channels. The user may be notified once a channel is sufficient so as to be suited for use in safety and security, and in what type of safety and security application it is suited for use.

By way of non-limiting example, true human authentication may simply assure that a biological human is present. This type of verification may be used for internet, gaming and entertainment applications, or for high-level social media and other online transactions.

Specific human identification may assure that a "specific" human is present. This can be used for identifying a certain person, such as for device security, banking, voting, and/or other sensitive transactions where confirming someone's identity with a high degree of confidence is required. In some embodiments, one or more of the authenticating mechanisms allows for the initiation and maintenance of an ongoing chain of custody of the mobile device by the authenticated user.

System activation using personally-identifiable information may also be provided. This may ensure that the system only responds to the commands from the authentic user tied to that device, i.e., the person that has performed an initial set-up of their profile with a certain number of biometrics (voice, face, palm, eyes, etc.) for that device, individually or in parallel.

Enabled by at least the baseline layer of biometric safety and security data, the system may continue to collect the aforementioned data from the various biometrics channels, as well as from the user's general use of the mobile phone (social media activity, content watching, communication via phone calls and email) as discussed throughout, in parallel. Ultimately, once sufficient data is accrued, the device may then uniquely make the determination on whether the user is holding, improving or deteriorating in mental or behavioral health, as discussed throughout. This may thus allow the system to infer the presence/absence/severity of, for example, Parkinsons (sensed symptoms such as drooling, mask-like facial expressions, slowed movements, walking gait, rigidity or stiffness, blinking less often than previously, etc.), Alzheimer's (sensed symptoms may include memory loss, decline in reasoning or language, changes in mood and coordination over time, etc.), and/or other behavioral-health issues (symptoms may include inattentiveness, hyperactivity or impulsiveness, feeling sad or down, difficulty concentrating, extreme mood swings, withdrawing from friends and activities, delusions or hallucinations, difficulty coping with stress, problems with alcohol or drugs, suicidal thoughts, etc.).

Of course, the device can also refine its ratings and/or its understanding of the user, either with or without direction to do so from the user. This refinement may or may not necessitate training, such as using the libraries discussed throughout. By way of example, the user may wish the device to not simply classify a mental state as negative-sad, but rather the user may wish the device to delineate the sadness as grieving vs. depression vs. loneliness.

Figure 7:
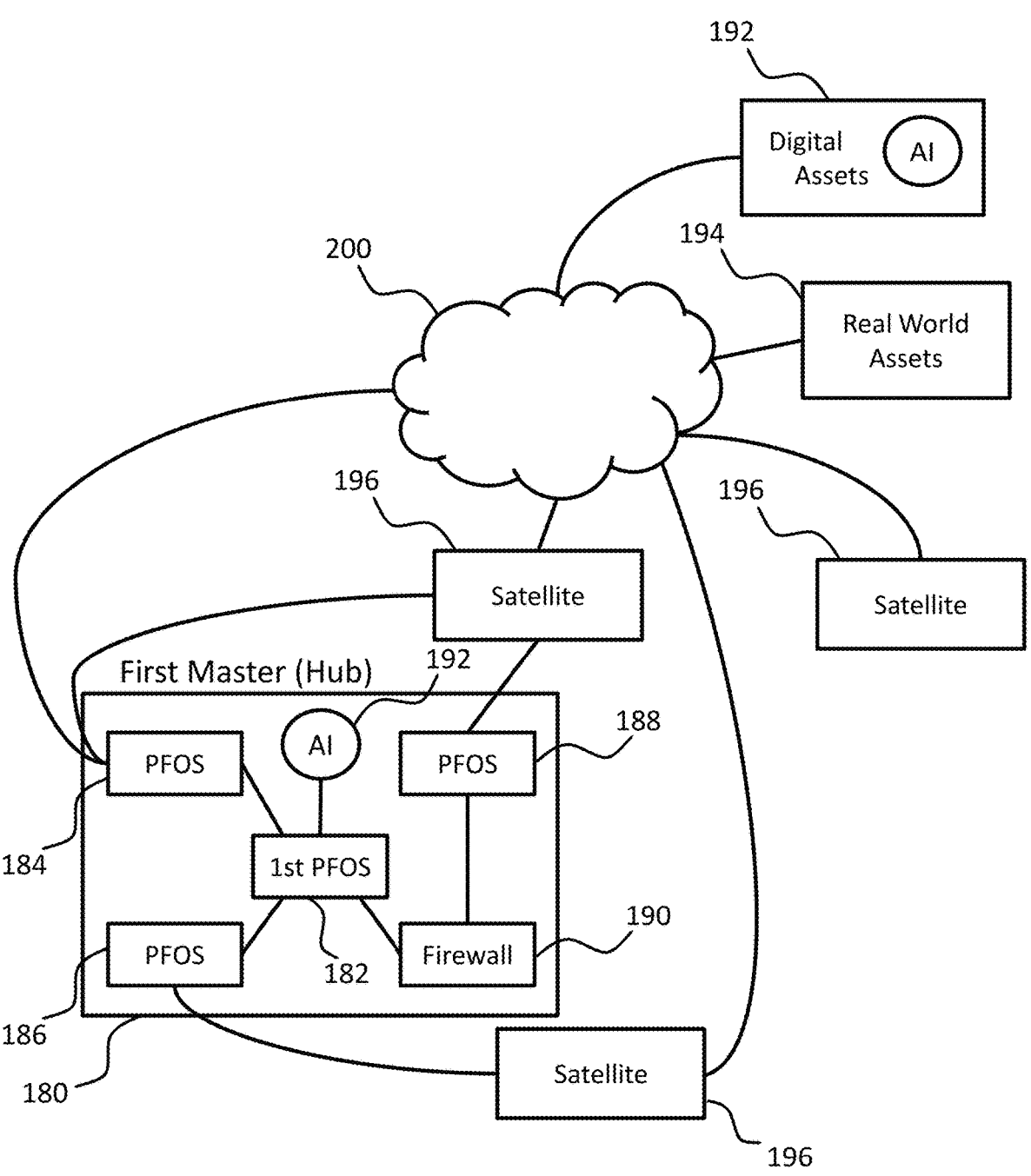
FIG. 7 graphically illustrates aspects of the disclosure.

FIG. 7 is an exemplary illustration of an embodiment, as discussed throughout, having a master processor/OS in the form of a first master device, i.e., a mobile or stationary device, server, server farm, or plurality of computing devices, interacting with a plurality of slave devices/OS's in the form of a plurality of satellite devices that are "enslaved" to the first master device. That is, the first master device may be capable of executing its own commands, or may have aspects of the first master device execute commands received from other aspects of the first master device, or the first master device may have satellite slave devices execute its commands and/or return information to the first master device.

In the illustration of FIG. 7 and more specifically as referenced throughout, the first master device 180 is, by way of example, a plurality of computing devices, at least one of which are insulated from any outside network, and at least one of which is connective to at least one outside network 200, such as the cloud, Wi-Fi, cellular, WLAN, LAN, Bluetooth, or like-networks, and through which the at least one non-connected first master device 180 may communicated outwardly using the connected network of the connected device. The connected device(s), correspondingly, do not have access to the personal avatar information of the one or more users of the first master device. That is, the non-connected one of the first master devices is "insulated" from the outside world, as discussed, and for the reasons discussed, throughout.

In an example, the first master device 180 may be comprised of 5 independent computing devices—2 of which may be connected (182, 184), 2 of which may be non-connected (186, 188), and 1 of which may provide the requisite firewalling management (190) to manage the secure information/personal avatar information discretely for each person managed by that first master device 180. That is, the firewalling capabilities of the first master device(s) 180 may not only manage data security and/or privacy for the personal avatar of a single user, but may additionally allow for the management of data security and/or privacy as between multiple users all using the first master device 180. Thus, for each user, the first master device 180 may provide both individualized personal avatars, and personal guardian angels of health, safety, privacy and security, which are individualized to each user on that first master device.

Both the connected and non-connected first master devices may have access to artificial intelligence (AI) capabilities 192 discussed throughout. These AI capabilities 192 may be "tunneled" to and from outside communication, in the manner of a virtual private network, via the connected ones of the first master devices 180 in order to maintain data security and/or privacy of the personal avatar information, which data security and/or privacy is managed by any firewalling devices 190 included among the first master devices 180. Furthermore, the first master device 180 may be capable of controlling "outside" AI apps to gain additional insight and information, such as Chat GPT. For example, digital assets 194 connected to outside network 200 and comprising AI, and or real world assets 194, also connected to outside network 200.

As discussed throughout, the ability for data to "tunnel" to and from the first master device(s) 180, or between connected and non-connected ones of the first master devices 180, may be controlled by biometrics. In the embodiments throughout, biometrics may be whatever a given device is capable of sensing, and may be varied by the first master device 180 based on that knowledge. Pointedly, if a satellite device 196 can only sense one of a palm, face, voice, fingerprint, heartrate, and so on, the hub will recognize that is what the satellite device 196 is capable of sensing, and will apply security and/or privacy protocols for access accordingly using that biometric element and based on its detailed knowledge of the user in the form of the personal avatar.

As such, the first master device(s) 180 may provide a multi-functional, multi-processor "hub" that serves as the master in the master-slave system discussed throughout; and further, some aspects of the hub, and particularly those aspects unconnected directly to outside networks, may serve as the master to other aspects of the hub. And unlike known "in-home hubs", the unconnected and firewalled nature of the disclosed hub allows it to have insight into every aspect of the user's life, both electronic and real-world, with permissions from the user. This deep insight allows the creation of the digital personal avatar discussed throughout, which enables the embodiments to give better information and answers to the users questions, and provide better information to both meet and anticipate the user's needs.

Indeed, the personal avatar includes all information, and summary information, of every day in the life of the user. Thus, the personal avatar understands and deconstructs the rich data generated in every life daily, based on the context of the experiences leading to the data. This "data" may include work v. play; stress v. relaxation; screen time; personal relationships (knows your mom, your dog, and your husband, just as you would); life balance; life goals; employment needs; and recommendations on how to make the user's life better in each of these areas, every day. Simply put, every person creates a tremendous volume of "data", both in the real and digital worlds, every day, and this data goes uncaptured in the known art, but is not only captured but is used in the embodiments to improve every aspect of the user's life.

To enable this life-improvement, the hub may break information into inner-dialog (solely user-centric) data; private dialog (i.e., information exchanged with or known to friends, family, or those others closest to the user) data; and public dialog (i.e., information known to or available to members of the public, including those outside the user's closest circle) data. This may provide a master hierarchy system that allows for categorization and sub-categorization of all user data, user needs, and user requests. This categorization may allow for both active and passive addressing of user needs, by category, per the user's preferences.

By way of example, the hub may recognize that the user is driving long past the user's typical bedtime, biometrics may indicate the user is very tired, and a mapping app may indicate that the user is still 6 hours from her destination. Accordingly, as the user may have authorized the hub to actively address needs that directly relate to the user's safety and health per the user's inner dialog, the hub may actuate both mapping apps and preferred hotel apps to find hotels along the route in the next 15 minutes that meet the user's known preferences—luxury bedding, big screen tv, and a full tub, for example—and may suggest that the user allow the hub to book one of the three most preferred options.

On the other hand, the user may be at a friend's birthday party and be perfectly fine, health-wise, such that the hub does not anticipate any need and is thus categorically passive. However, the hub may spring to action when the user suddenly says "Get me a cab ASAP". The hub now knows that the user prefers a luxury car, with mood lighting and jazz playing, and that the user had an argument with his boss at work today, and thus is willing to pay for the preferred luxurious and relaxing cab environment.

Thus, the insulated, secure knowledge of the personal avatar may allow for a layered approach to addressing needs and requests. For example and as referenced above, the personal avatar of the user may share the user's needs—for example, a need for love, a need for protection, and a need for a job. The user's personal avatar may then interview and/or develop relationships with the personal avatars of other users in an attempt to find real-world people to fulfill these user wants/needs. Simply put, if the personal avatars develop the desired relationship, then it is likely that the real world people that those avatars reflect are highly likely to also develop the desired relationship. Accordingly, the avatars may, or may not be instructed to, develop relationships in a manner and at a rate comfortable to their respective users, based on intimate knowledge of the respective users.

As referenced immediately above, the hub may thus have access to nearly unlimited outside software and apps to act on behalf of, and indeed "act on behalf" of the user's consent, including the aforementioned cab/Uber/Lyft apps to order a car/cab, Marriott, Hilton, Expedia, or similar apps, and Waze, Apple Maps, and similar navigation apps. Likewise, the hub may avail itself of new apps heretofore unknown, such as inner dialog apps v. private dialog apps, as those terms are used above. These new app-types may be placed in an app store on or accessible to the hub, by way of example. Such apps may include, by way of non-limiting example: completely secure password management apps (which don't require the user to ever enter or store usernames or passwords, but which instead just learns them organically and associates them with the verified user); certification apps, such as may certify mental health (based on knowledge of the personal avatar) such as for purchase of a gun; or apps for assisting with certain health conditions based on the pre-existing knowledge about the user embedded in the personal avatar, such as apps to help those developing senile dementia.

Apps may also be provided that are uniquely tailored to the personal avatar, i.e., to the user, in ways not presently available using the known art. For example, entertainment apps may be provided which gamify biometrics, or which gamify mental faculties. Such tailored apps may be used in conjunction with external hardware, such as a "sensory booth". By way of example, a virtual haunted house may be provided in a sensory booth, where the experience is tailored to that which is scariest (or least scary, at the option of the user) based on the knowledge of the personal avatar and biometric sensing. Of course, such experiences may also be tailored in the real world uniquely to each user, also based on the knowledge of the personal avatar.

Similarly, the apps/actions provided by the hub may be comparable those features already offered, such as by mobile devices, but with significant modifications based on the creation of the personal avatar. For example, a user may be enabled to silence notifications in the embodiments, as the user can do presently on any mobile device; but this feature may be enhanced with nuance regarding the silencing. By way of further example, the user may indicate that she is in a meeting, and thus notifications should be silenced; however, the user may nevertheless request the playing of a certain tone, or the displaying of a doorbell on a screen, when her daughter arrives home from school.

Yet further, known actions, such as consent, may now be uniquely tailored using the embodiments. For example, current apps/sites may gain consent of a user for use thereof through a lengthy, standard click-thru contractual consent. In the embodiments, this consent may now be interactive and informed in ways to which the user is known to be particularly amenable.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. To make and use the disclosed aspects, various modifications to the disclosure will be readily apparent to those skilled in the art. Further, any generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed and claimed as follows.

What is claimed is:

1. A system, comprising:
a plurality of satellite slave processors associated with satellite devices, each having operatively communicative therewith a dedicated operating system (DOS) comprising non-transitory computing code;
at least one first master device including at least one personal functions processor having operatively communicative therewith a personal functions operating system (PFOS) comprising non-transitory computing code;
at least one of the PFOS being capable of commanding the DOS, and thereby being capable of accessing and controlling applications data provided by the satellite slave processors, the applications data including:
biometrics sensor data;
a plurality of authentication mechanisms authenticating at least a presence of and specific identity of a human user; and
a plurality of the applications data comprising well-being applications data responsive to the human user only upon a valid one of the authenticating,
wherein the PFOS capable of commanding the DOS is communicatively insulated from communications networks accessed by the DOS.

2. The system of claim 1, wherein the communications network is at least one of a cloud network, Wi-Fi, cellular, WLAN, LAN, or Bluetooth.

3. The system of claim 1, wherein solely the at least one PFOS capable of commanding the DOS has accessible thereto a personal avatar of a user formed from processed output of the biometrics sensor data, the plurality of authentication mechanisms, and the plurality of the applications data.

4. The system of claim 3, wherein at least one of the DOS comprises firewalling capabilities for the system.

5. The system of claim 3, wherein the personal avatar comprises multiple personal avatars uniquely corresponded to each of multiple ones of the user, and wherein the firewalling capabilities discretize the multiple personal avatars for access only by a uniquely corresponded one of the users.

6. The system of claim 1, wherein the well-being is at least one of health, privacy, safety and security.

7. The system of claim 6, wherein the health is at least one of mental, emotional and physical.

8. The system of claim 1, wherein the well-being is knowledge of likes and dislikes to enable provision of services from secondary applications which are individualized to each user on that first master device.

9. The system of claim 1, wherein the well-being applications comprise artificial intelligence (AI) capabilities.

10. The system of claim 9, wherein the biometric sensor data controls all access to the well-being applications.

11. The system of claim 10, wherein the biometrics sensor data is dependent on biometric capabilities of each of the satellite devices.

12. The system of claim 11, wherein the biometrics capabilities comprise at least one of scanning of the user's eye(s), ears(s), palm, face, footprint, skin, voice, fingerprint, and heartrate.

13. The system of claim 10, wherein the personal avatar comprises all aspects of a user's life, both digital and real-world.

14. The system of claim 13, wherein data learned by the well-being applications includes at least work v. play time, stress v. relaxation time, screen time; scrolling patterns; personal relationships, emotional balance, life goals, likes and dislikes, employment needs, to facilitate one or more of Socratic dialog, relevance realization, and recommendations on life improvement.

15. The system of claim 10, wherein data comprising the personal avatar comprises inner-dialog data, private dialog data, and public dialog data.

16. The system of claim 15, wherein the inner dialog, private dialog and public dialog data provides a categorization and sub-categorization system for all user data, user needs, and user requests.

17. The system of claim 16, wherein this categorization system allows for both active and passive addressing of user needs, by category, per user preferences.

18. The system of claim 17, wherein the active addressing comprises addressing the user needs absent specific instructions from the user.

19. The system of claim 17, wherein the passive addressing comprises addressing the user needs responsive to specific instructions from the user.

20. The system of claim 19, wherein the passive addressing includes addressing in a manner considering the user preferences not included in the specific instructions.

21. The system of claim 1, further comprising a network of personal avatars developed by the PFOS capable of commanding the DOSs, each of the network of personal avatars being indicative of a distinct user of the system, wherein the personal avatars interact in digital space absent specific control from each of the distinct users.

22. The system of claim 21, wherein the interaction of the personal avatars in digital space is indicative of a nature of interactions of the distinct users in a real world space.

23. The system of claim 1, wherein one or more of the authenticating mechanisms allows for the initiation and maintenance of an ongoing chain of custody of the mobile device by the authenticated user.

24. The system of claim 1, wherein one of the well-being apps is an informed consent app for gaining a user's informed consent for others of the plurality of applications.

25. The system of claim 1, wherein the well-being applications comprise certification applications for at least one of physical, mental and emotional well-being.

\* \* \* \* \*